United States Patent
Freeman et al.

(10) Patent No.: US 7,959,857 B2
(45) Date of Patent: Jun. 14, 2011

(54) RADIATION STERILIZATION OF MEDICAL DEVICES

(75) Inventors: Abigail Freeman, Fremont, CA (US);
Brian Riggs, Temecula, CA (US);
Robert Harrison, Perris, CA (US);
Greg Simmons, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 11/809,511

(22) Filed: Jun. 1, 2007

(65) Prior Publication Data
US 2008/0299002 A1    Dec. 4, 2008

(51) Int. Cl.
*A61L 2/00* (2006.01)
*B01J 19/08* (2006.01)
*G01T 1/185* (2006.01)
*G01N 21/00* (2006.01)
*H01J 27/00* (2006.01)
*A61B 6/00* (2006.01)
*A61B 5/00* (2006.01)
*A61M 29/00* (2006.01)

(52) U.S. Cl. ......... 422/22; 422/1; 422/186.05; 250/389; 250/427; 250/433; 250/453.11; 250/455.11; 250/492.3; 250/515.1; 600/434; 600/585; 606/191; 606/194; 606/198

(58) Field of Classification Search ............... 422/1, 22, 422/186.05; 250/389, 427, 433, 453.11, 250/455.11, 492.3, 515.1; 600/434, 585; 606/191, 194, 198
See application file for complete search history.

(56) References Cited

U.S. PATENT DOCUMENTS

| | | | |
|---|---|---|---|
| RE23,195 E * | 2/1950 | Brasch | ........................ 21/54 |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |

(Continued)

FOREIGN PATENT DOCUMENTS

DE       44 07 079       9/1994

(Continued)

OTHER PUBLICATIONS

U.S. Appl. No. 10/317,435, filed Dec. 11, 2002, Hossainy et al.

(Continued)

*Primary Examiner* — Jill Warden
*Assistant Examiner* — Monzer R Chorbaji
(74) *Attorney, Agent, or Firm* — Squire, Sanders & Dempsey (US) LLP

(57) ABSTRACT

Disclosed herein is a method of radiation sterilizing a plurality of medical devices.

45 Claims, 11 Drawing Sheets

U.S. PATENT DOCUMENTS

| | | | |
|---|---|---|---|
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,800,882 A | 1/1989 | Gianturco | |
| 4,816,339 A | 3/1989 | Tu et al. | |
| 4,818,559 A | 4/1989 | Hama et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury et al. | |
| 5,356,433 A | 10/1994 | Rowland et al. | |
| 5,383,925 A | 1/1995 | Schmitt | |
| 5,385,580 A | 1/1995 | Schmitt | |
| 5,389,106 A | 2/1995 | Tower | |
| 5,399,666 A | 3/1995 | Ford | |
| 5,423,885 A | 6/1995 | Williams | |
| 5,441,515 A | 8/1995 | Khosravi et al. | |
| 5,443,458 A | 8/1995 | Eury et al. | |
| 5,443,500 A | 8/1995 | Sigwart | |
| 5,455,040 A | 10/1995 | Marchant | |
| 5,464,650 A | 11/1995 | Berg et al. | |
| 5,502,158 A | 3/1996 | Sinclair et al. | |
| 5,514,379 A | 5/1996 | Weissleder et al. | |
| 5,527,337 A | 6/1996 | Stack et al. | |
| 5,545,408 A | 8/1996 | Trigg et al. | |
| 5,554,120 A | 9/1996 | Chen et al. | |
| 5,556,413 A | 9/1996 | Lam | |
| 5,578,046 A | 11/1996 | Liu et al. | |
| 5,578,073 A | 11/1996 | Haimovich et al. | |
| 5,591,199 A | 1/1997 | Porter et al. | |
| 5,591,607 A | 1/1997 | Gryaznov et al. | |
| 5,593,403 A | 1/1997 | Buscemi | |
| 5,593,434 A | 1/1997 | Williams | |
| 5,599,301 A | 2/1997 | Jacobs et al. | |
| 5,599,922 A | 2/1997 | Gryaznov et al. | |
| 5,605,696 A | 2/1997 | Eury et al. | |
| 5,607,442 A | 3/1997 | Fischell et al. | |
| 5,607,467 A | 3/1997 | Froix | |
| 5,618,299 A | 4/1997 | Khosravi et al. | |
| 5,629,077 A | 5/1997 | Turnlund et al. | |
| 5,631,135 A | 5/1997 | Gryaznov et al. | |
| 5,632,771 A | 5/1997 | Boatman et al. | |
| 5,632,840 A | 5/1997 | Campbell | |
| 5,637,113 A | 6/1997 | Tartaglia et al. | |
| 5,649,977 A | 7/1997 | Campbell | |
| 5,667,767 A | 9/1997 | Greff et al. | |
| 5,667,796 A | 9/1997 | Otten | |
| 5,670,558 A | 9/1997 | Onishi et al. | |
| 5,693,085 A | 12/1997 | Buirge et al. | |
| 5,700,286 A | 12/1997 | Tartaglia et al. | |
| 5,707,385 A | 1/1998 | Williams | |
| 5,711,763 A | 1/1998 | Nonami et al. | |
| 5,716,981 A | 2/1998 | Hunter et al. | |
| 5,725,549 A | 3/1998 | Lam | |
| 5,726,297 A | 3/1998 | Gryaznov et al. | |
| 5,728,751 A | 3/1998 | Patnaik | |
| 5,733,326 A | 3/1998 | Tomonto et al. | |
| 5,733,330 A | 3/1998 | Cox | |
| 5,733,564 A | 3/1998 | Lehtinen | |
| 5,733,925 A | 3/1998 | Kunz et al. | |
| 5,741,881 A | 4/1998 | Patnaik | |
| 5,756,457 A | 5/1998 | Wang et al. | |
| 5,756,476 A | 5/1998 | Epstein et al. | |
| 5,765,682 A | 6/1998 | Bley et al. | |
| 5,766,204 A | 6/1998 | Porter et al. | |
| 5,766,239 A | 6/1998 | Cox | |
| 5,766,710 A | 6/1998 | Turnlund et al. | |
| 5,769,883 A | 6/1998 | Buscemi et al. | |
| 5,780,807 A | 7/1998 | Saunders | |
| 5,800,516 A | 9/1998 | Fine et al. | |
| 5,811,447 A | 9/1998 | Kunz et al. | |
| 5,824,049 A | 10/1998 | Ragheb et al. | |
| 5,830,178 A | 11/1998 | Jones et al. | |
| 5,830,461 A | 11/1998 | Billiar et al. | |
| 5,830,879 A | 11/1998 | Isner | |
| 5,833,651 A | 11/1998 | Donovan et al. | |
| 5,834,582 A | 11/1998 | Sinclair et al. | |
| 5,836,962 A | 11/1998 | Gianotti | |
| 5,837,313 A | 11/1998 | Ding et al. | |
| 5,837,835 A | 11/1998 | Gryaznov et al. | |
| 5,840,083 A | 11/1998 | Braach-Maksvytis | |
| 5,851,508 A | 12/1998 | Greff et al. | |
| 5,853,408 A | 12/1998 | Muni | |
| 5,854,207 A | 12/1998 | Lee et al. | |
| 5,855,612 A | 1/1999 | Ohthuki et al. | |
| 5,855,618 A | 1/1999 | Patnaik et al. | |
| 5,858,746 A | 1/1999 | Hubbell et al. | |
| 5,865,814 A | 2/1999 | Tuch | |
| 5,868,781 A | 2/1999 | Killion | |
| 5,873,904 A | 2/1999 | Ragheb et al. | |
| 5,874,101 A | 2/1999 | Zhong et al. | |
| 5,874,109 A | 2/1999 | Ducheyne et al. | |
| 5,874,165 A | 2/1999 | Drumheller | |
| 5,876,743 A | 3/1999 | Ibsen et al. | |
| 5,877,263 A | 3/1999 | Patnaik et al. | |
| 5,879,713 A | 3/1999 | Roth et al. | |
| 5,888,533 A | 3/1999 | Dunn | |
| 5,891,192 A | 4/1999 | Murayama et al. | |
| 5,897,955 A | 4/1999 | Drumheller | |
| 5,906,759 A | 5/1999 | Richter | |
| 5,914,182 A | 6/1999 | Drumheller | |
| 5,916,870 A | 6/1999 | Lee et al. | |
| 5,922,005 A | 7/1999 | Richter et al. | |
| 5,942,209 A | 8/1999 | Leavitt et al. | |
| 5,948,428 A | 9/1999 | Lee et al. | |
| 5,954,744 A | 9/1999 | Phan et al. | |
| 5,957,975 A | 9/1999 | Lafont et al. | |
| 5,965,720 A | 10/1999 | Gryaznov et al. | |
| 5,971,954 A | 10/1999 | Conway et al. | |
| 5,976,182 A | 11/1999 | Cox | |
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,986,169 A | 11/1999 | Gjunter | |
| 5,997,468 A | 12/1999 | Wolff et al. | |
| 6,010,445 A | 1/2000 | Armini et al. | |
| 6,015,541 A | 1/2000 | Greff et al. | |

| | | | |
|---|---|---|---|
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,806,476 B2 * | 10/2004 | Rose et al. ............... 250/455.11 |
| 6,818,063 B1 | 11/2004 | Kerrigan |
| 6,846,323 B2 | 1/2005 | Yip et al. |
| 7,166,099 B2 | 1/2007 | Devens, Jr. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0065355 A1 | 4/2003 | Weber |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen et al. |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0215354 A1 * | 11/2003 | Clark et al. ............... 422/22 |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |
| 2005/0013729 A1 * | 1/2005 | Brown-Skrobot et al. ..... 422/24 |
| 2005/0233062 A1 * | 10/2005 | Hossainy et al. ............ 427/2.1 |
| 2006/0067974 A1 * | 3/2006 | Labrecque et al. .......... 424/426 |
| 2007/0065334 A1 | 3/2007 | Shalaby |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 218 003 | 4/1987 |
| EP | 0 364 787 | 4/1990 |
| EP | 0 397 500 | 11/1990 |
| EP | 0 464 755 | 1/1992 |
| EP | 0 493 788 | 7/1992 |

| | | |
|---|---|---|
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| JP | 11 133196 | 5/1999 |
| JP | 2000 334028 | 12/2000 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 03/037390 | 5/2003 |
| WO | WO 2004/023985 | 3/2004 |
| WO | WO 2006/034157 | 3/2006 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

nanoComposix, products, www.nanocomposix.com, downloaded Mar. 26, 2007, 2 pgs.

Nanosiliver, Photocatalyst and Nanocomposite Material, http://eng.nanocomposite.net downloaded Mar. 26, 2007, 1 pg.

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal—results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

International Search Report for PCT/US2007/0129930 filed Jun. 1, 2007, mailed Dec. 18, 2007, 5 pgs.

Pending U.S. Appl. No. 11/803,829.

\* cited by examiner

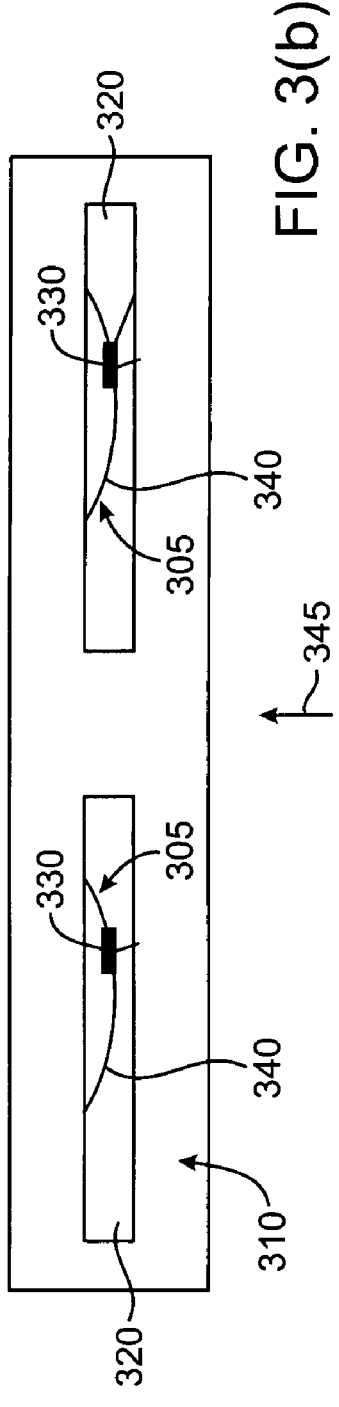
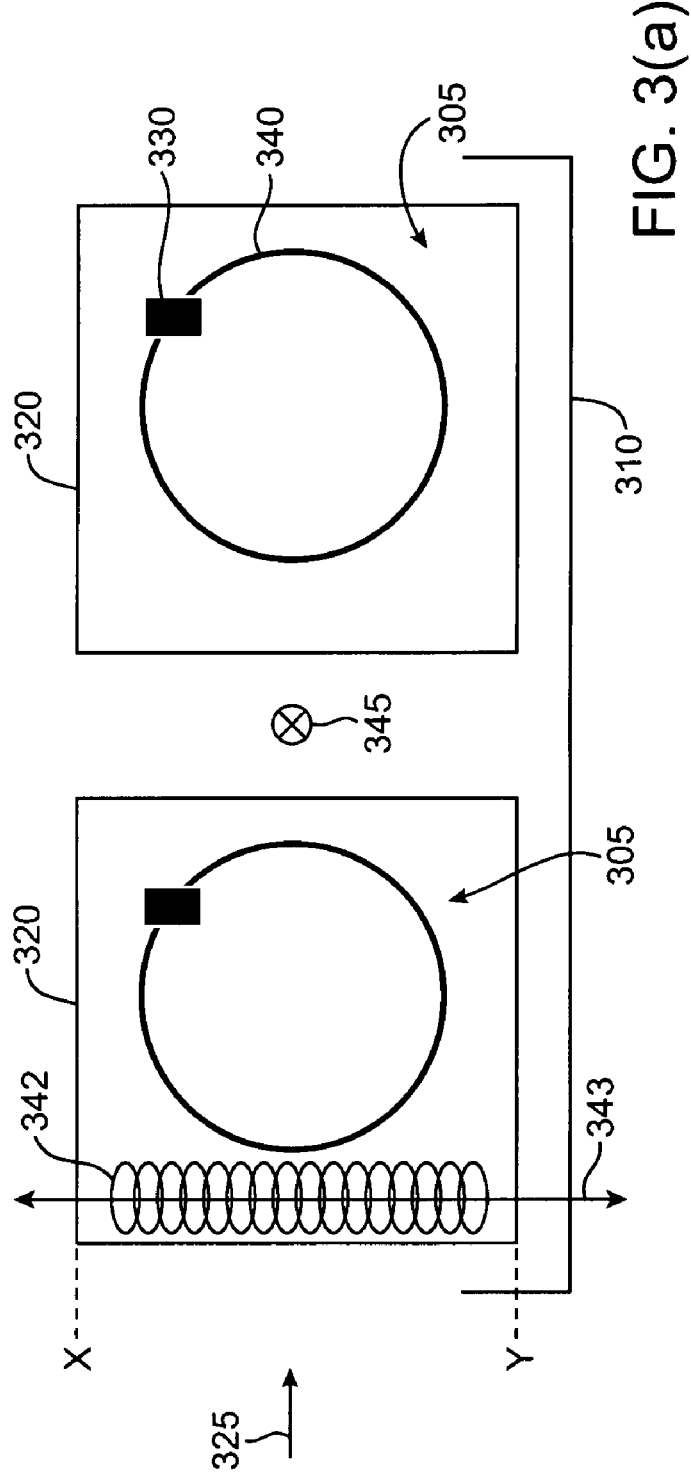

RADIATION STERILIZATION OF MEDICAL DEVICES

BACKGROUND OF THE INVENTION

1. Field of the Invention

Disclosed herein are methods and apparatuses for sterilization of medical devices using radiation.

2. Description of the State of the Art

Disclosed herein are radially expandable endoprostheses adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. The polymeric scaffolding may also serve as a carrier of an active agent or drug.

After a stent is fabricated, a stent or a stent-catheter device typically undergoes sterilization to reduce the bioburden of the stent to an acceptable sterility assurance level (SAL). There are numerous methods of sterilizing medical devices such as stents, the most common being ethylene oxide treatment and treatment with ionization radiation such as electron beam (E-beam) and gamma radiation.

There is a desire to make E-beam sterilization commercially feasible for polymeric stents. As medical devices increase in complexity, sterilization process technology becomes imperative. A commercially feasible E-beam sterilization process that is compatible with existing E-beam facilities is desired. Also desired is a fixture apparatus having the capability of processing a large volume of medical devices in a short period of time, robustness to human error, and reproducibility of dose from device to device.

SUMMARY

Various embodiments of the present invention include a method of radiation sterilizing a plurality of stent-catheter assemblies, the method comprising: positioning a plurality of stent-catheter assemblies on a fixture, each of the stent catheter assemblies being arranged in a planar configuration and disposed in corresponding planar packages supported on the fixture, wherein the packages are stacked horizontally on the fixture; and exposing the packages to an incoming radiation beam, the radiation beam being at an acute angle to the planes of the planar configuration of the assemblies, wherein the packages are arranged such that a front end of the stack faces the radiation beam and a back end of the stack faces away from the radiation beam.

Further embodiments of the present invention include a method of radiation sterilizing a plurality of medical devices, the method comprising: positioning a plurality medical devices on a fixture; and exposing the devices to an incoming radiation beam through movement of the plurality of devices with respect to a radiation source, wherein the number of devices through which the radiation beam passes varies with the movement, wherein a radiation shield is positioned such that a variation in radiation exposure among the medical devices from incoming or backscattered radiation is reduced.

BRIEF DESCRIPTION OF THE DRAWINGS

FIG. 3(a) is a schematic illustration of a front view of a fixture for supporting two packages, each package containing a stent-catheter assembly.

FIG. 3(b) depicts an overhead view of a fixture of FIG. 3(a).

DETAILED DESCRIPTION OF THE INVENTION

Radiation sterilization is well known to those of ordinary skill in the art. Medical devices composed in whole or in part of polymers can be sterilized by various kinds of radiation, including, but not limited to, electron beam (E-beam), gamma ray, ultraviolet, infra-red, ion beam, x-ray, and laser sterilization. Generally, it is desirable to increase the throughput of sterilization processes to increase the manufacturing efficiency.

Various embodiments of the present invention relate to the sterilization of multiple medical devices. Such medical devices include implantable medical devices and delivery systems for such devices. The methods described herein may be applied generally to polymeric implantable medical devices, such as for stents, in particular polymeric stents. The methods reduce or narrow the range of radiation exposure from device to device.

Therefore, each device may be irradiated within a specified or selected range. This is of particular importance for polymeric devices, since exposure to radiation above a specified range can cause undesirable degradation of chemical and mechanical properties of a polymer. The methods discussed herein reduce the likelihood of irradiation outside a specified range, causing an undesirable increase in temperature and a corresponding undesirable degree of degradation.

The methods disclosed herein may be applied in combination with a reduced temperature sterilization process in which a device is cooled before, during, and/or after sterilization. The reduced temperature can be below ambient temperature during sterilization. The methods disclosed herein may be applied to a sterilization process using various kinds of radiation.

Examples of implantable medical devices include, but are not limited to, self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

Figure 1:
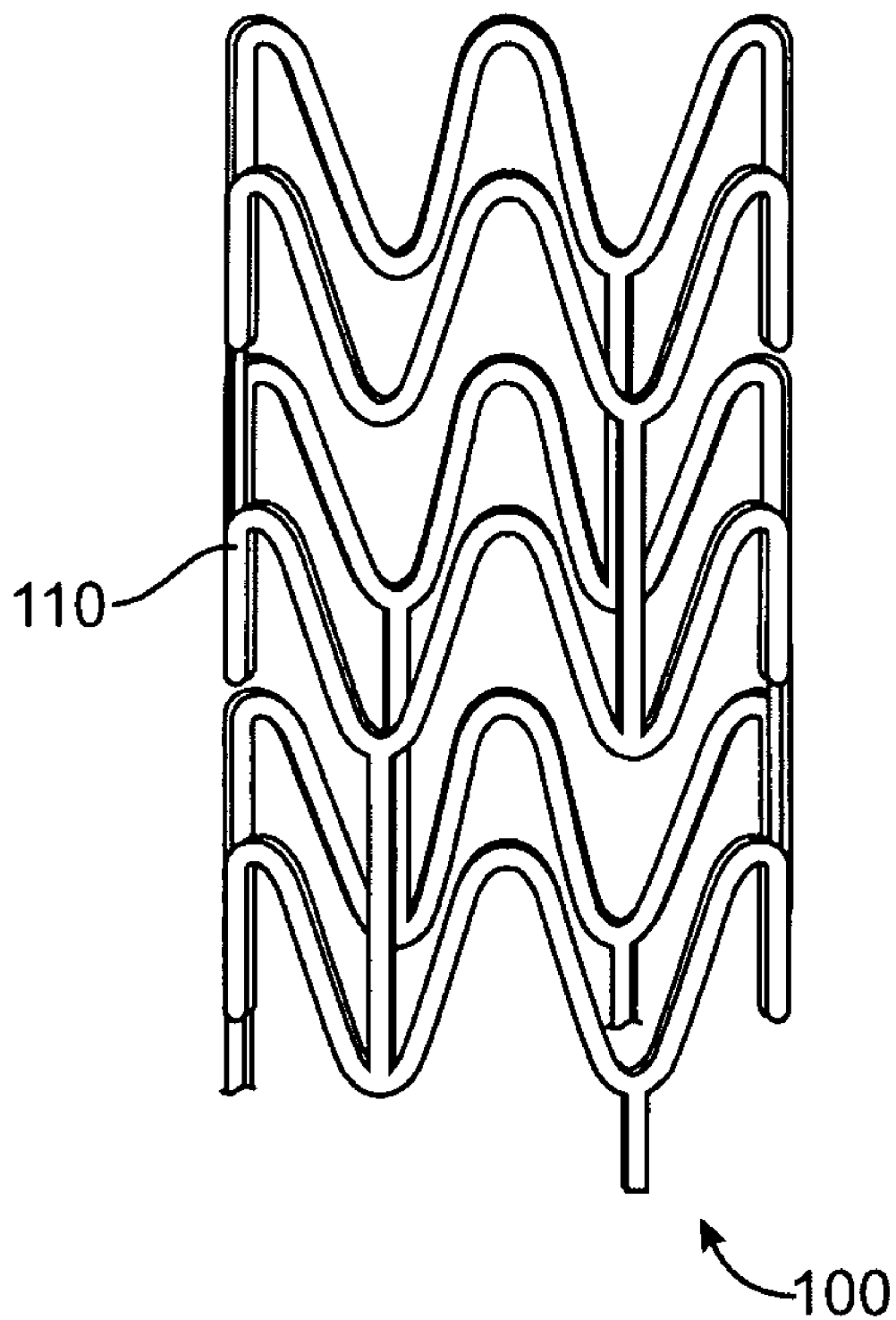
FIG. 1 depicts an example of a stent.

FIG. 1 depicts an example of a stent 100. Stent 100 has a cylindrical shape and includes a pattern with a number of interconnecting structural elements or struts 110. In general, a stent pattern may be designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

Sterilization is typically performed on implantable medical devices, such as stents and catheters, to reduce the bioburden on the device. Bioburden refers generally to the number of microorganisms that contaminate an object. The degree of sterilization is typically measured by a Sterility Assurance Level ("SAL"), referring to the probability of a viable microorganism being present on a device unit after sterilization. A sterilization dose can be determined by selecting a dose that provides a required "SAL". The required SAL for a device is dependent on the intended use of the device. For example, a device to be used in the body's fluid path is considered a Class III device. SALs for various medical devices can be found in materials from the Association for the Advancement of Medical Instrumentation (AAMI) in Arlington, Va. In one embodiment, the sterility assurance level for biodegradable stents is at a radiation dose from about 20 kGy to about 30 kGy.

Figure 2:
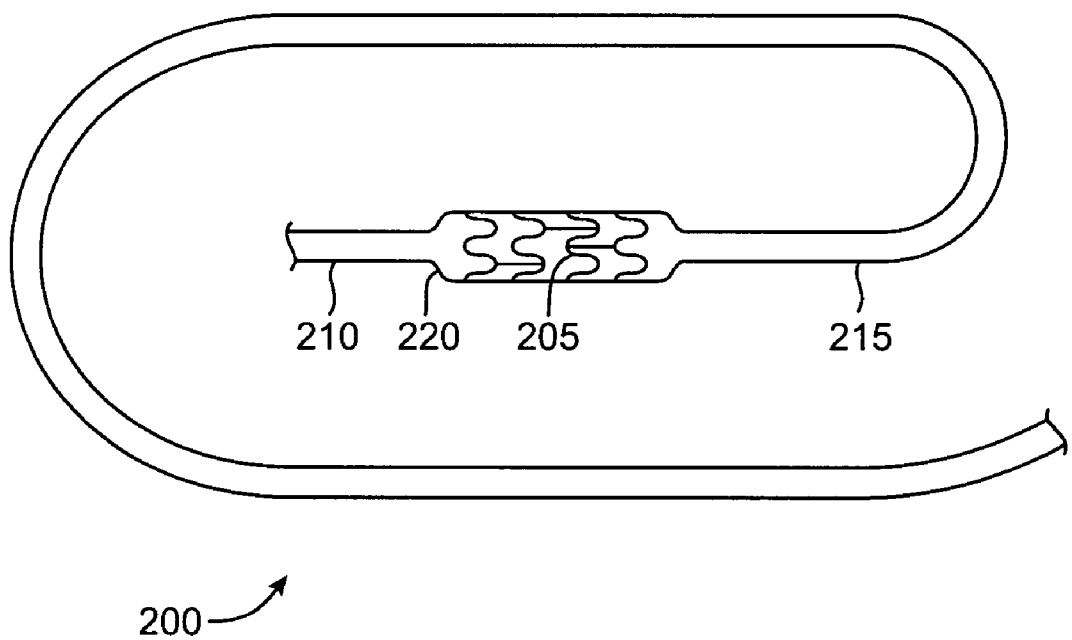
FIG. 2 depicts a stent-catheter assembly.

A stent is typically sterilized after being mounted onto a delivery system or device, such as a catheter. Stents are also typically sterilized, packaged, stored, and transported in a "ready to implant" configuration in which the stent is disposed at the distal end of a catheter. However, the methods described are not limited to sterilizing a mounted stent. FIG. 2 depicts a stent-catheter assembly 200 with a stent 205 disposed on a distal end 210 of a catheter 215. Stent 205 can be crimped over a balloon 220. Stent-catheter assembly 200 may be packaged prior to or after radiation sterilization. Various embodiments herein describe sterilization after stent-catheter assembly 200 is packaged.

The embodiments described herein may be used for sterilizing various kinds of devices, such as an implantable medical device, in particular a stent-catheter assembly. In one embodiment, the device, as described above, can also be enclosed in a container or package. The container or package can include a sealable flexible metallic or plastic pouch that is conventionally used for storage and shipping a stent-catheter assembly. Generally, the pouch protects the assembly from exposure to air, moisture, and light.

In an embodiment, a container or package of a stent-catheter assembly includes a chipboard box and a pouch that is disposed within the box. Typically, stent-catheter assemblies are sterilized after packaging by methods such as E-beam sterilization. A packaged stent-catheter assembly is supported on a fixture during sterilization. The fixture is typically moved on a conveyer arrangement past a radiation beam from a radiation source in a manner that the radiation beam is directed onto the stent-catheter assembly. Alternatively, the radiation source can be moved with respect to the fixture.

In a cold E-beam sterilization process, the stent-catheter assembly can be cooled prior to and/or after sterilization. Additionally or alternatively, the temperature of the stent-catheter assembly can be controlled at a reduced temperature during E-beam sterilization. The stent-catheter assembly can be cooled to a reduced temperature below an ambient temperature which can refer to a temperature between about 15-30° C. In various embodiments, reduced temperature can be less than 10° C., 0° C., −15° C., −25° C., −40° C., −70° C., −100° C., −150° C., −200° C., −240° C., or less than −270° C. The stent-catheter assembly can be cooled by various methods. For example, the cooling prior to sterilization can be performed by disposing the stent-catheter assembly in a freezer for a time sufficient to cool the stent-catheter assembly to a desired temperature.

FIG. 3(a) depicts a schematic illustration of a front view of a fixture 310 supporting two packages 320, each containing a stent-catheter assembly 305 having a stent 330 and catheter 340. Packages 320 can be, for example, a chipboard box containing the stent-catheter assembly disposed within a pouch. FIG. 3(b) depicts an overhead view of fixture 310 of FIG. 3(a) containing packages 320.

In some embodiments, fixture 310 in FIG. 3(b) can be moved as shown by an arrow 325 past a stationary E-beam source that directs an E-beam perpendicular to the face of packages 320, the face being perpendicular to the plane of the page. As shown, a beam 345 is directed perpendicular to the faces of packages 320. The cross-section of the E-beam is circular or generally circular in shape, as depicted by a pulse 342 of an E-beam. In such embodiments, the E-beam is moved up and down as shown by an arrow 343 to irradiate fixture 310 and assemblies 305 along an axis from position X to position Y. Thus, as fixture 310 is conveyed in the direction shown by arrow 325, the entire fixture and assemblies 305 can be irradiated. In some embodiments, the beam pulses up and down 50-70 times, or more narrowly, 64 times a second.

Figure 3C:
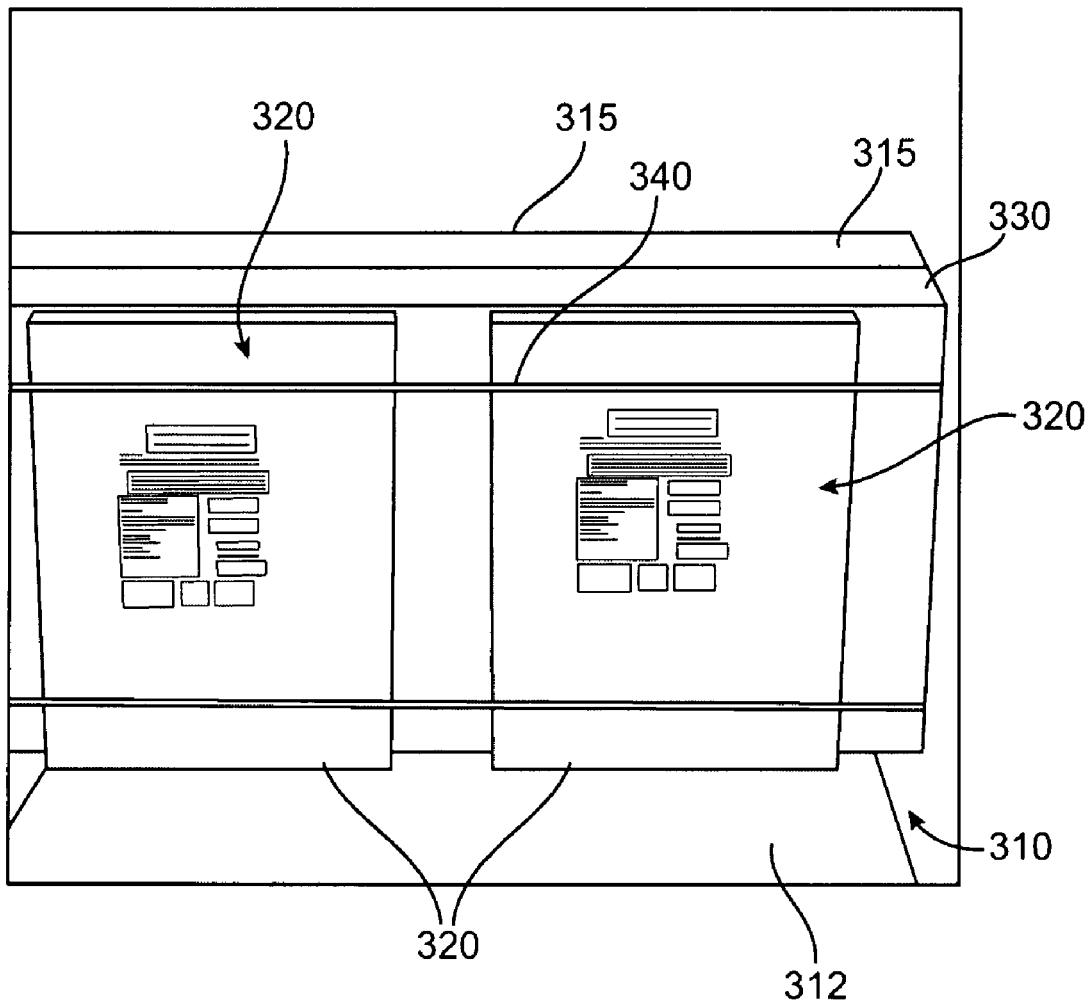
FIG. 3(c) depicts a photograph an overhead view of a fixture supporting two chipboard boxes.

FIG. 3(c) depicts a photograph of front view of fixture 310 supporting two chipboard boxes 320. Fixture 310 includes a metal plate 312 and a support arm 315 that supports boxes 320. Behind chipboard boxes 320 is a foam slab 330. Behind foam slab 330 is support arm 315 of fixture 310 that supports boxes 320. Chipboard boxes 320 are held onto support arm 315 of fixture 310 by fasteners 340. Chipboard boxes can include a stent-catheter assembly that is encased in a pouch (not shown).

In such an arrangement shown in FIGS. 3(a)-3(c), sufficient sterilization of the stent-catheter assembly 305 may require more than one pass past the radiation source. Thus, stent-catheter assemblies 305 can be irradiated with two passes, one pass for exposing one side of the assemblies, and the other pass for irradiating the other side of the assemblies.

With reference to FIG. 2, catheter 215 of stent-catheter assembly 200 may be able to sustain radiation exposure to 50 kGy since the performance of a catheter is less sensitive to radiation exposure. However, the performance of a stent, such as stent 205, is more sensitive to degradation by high radiation doses, in particular a stent having a polymer substrate and/or a polymer coating. High radiation doses can adversely affect the chemical and mechanical properties of a polymer in the stent which can affect its therapeutic functions. For example, if a dose of 25 kGy is desired to be delivered to the stent-catheter assembly 200, two doses of 12.5 kGy are delivered to the device per pass in order to avoid over-exposing the stent to radiation. After irradiating the first side with 12.5 kGy of radiation by focusing the E-beam directly on the package as described, the packages are flipped over to the other side, and irradiated with the remaining 12.5 kGy of radiation.

Sterilization of two devices with two passes of radiation is time consuming and thus, reduces manufacturing efficiency and throughput. An exemplary fixture may allow only two devices to be sterilized at a time using two passes, one for the front and the other for the back of the devices. The devices can be cooled prior to the second irradiation step to reduce or eliminate chemical and/or mechanical degradation of the polymer of the stent caused by high radiation doses. Thus, sterilization of two devices with two passes of radiation is even more time consuming when the devices must be cooled in between passes of radiation. In some embodiments, the cooling time can be several hours, for example, 12 hours. Thus, cooling before the first pass can be 12 hours, cooling after the first pass can be 12 hours, and cooling after the second pass can be 12 hours.

Additionally, it is desired to deliver a radiation dose to a device in a predictable, narrow range. In this way, reproducibility of the dosage from device to device may be achieved. As described above, one or two devices may be irradiated during one pass of radiation. Such methods of sterilization are limited in their capacity to deliver consistent doses with a narrow range of radiation exposure from device to device.

In the embodiments described herein, multiple devices can be irradiated and sufficiently sterilized with one pass of irradiation. In such embodiments, the orientation of the devices on the fixture in relation to the beam (e.g., the orientation of the face of the package in FIG. 3(a) with respect to the beam) and the position of radiation shields on the devices enable multiple devices (not just two) to be sterilized in one pass of radiation. Since multiple devices are sterilized in one pass, both processing time and throughput are increased compared to the methods illustrated in FIGS. 3(a)-(c). In addition, all of the devices on the fixtures are irradiated substantially uniformly, such that the range of the radiation dose from device to device is very narrow and consistent. Thus, reproducibility of radiation dose from device to device is increased. By increasing reproducibility of radiation dose, fewer devices fall outside a desired SAL range. Also, sterilizing multiple devices in one pass of radiation eliminates the need to cool the devices between passes, further reducing manufacturing time and increasing throughput.

Thus, the embodiments provide a method and apparatus for sterilizing multiple devices at once. Multiple devices are positioned on a fixture during the single pass of radiation so that all of the devices are exposed to a radiation in such a way that the radiation dose from device to device falls within a narrow range. As a result, the methods and apparatus provide good reproducibility from device to device.

Figure 4A:
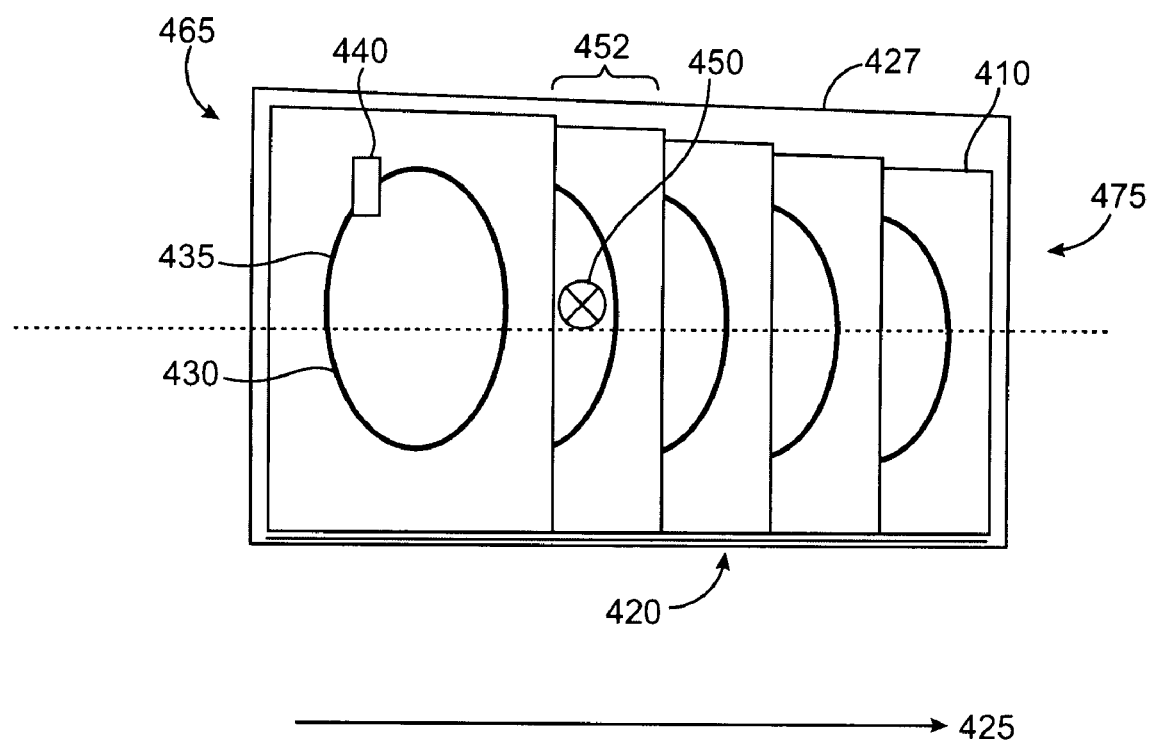
FIG. 4(a) depicts a schematic illustration of a front view of multiple packages supported by a fixture, each package containing a stent-catheter assembly.
Figure 4B:
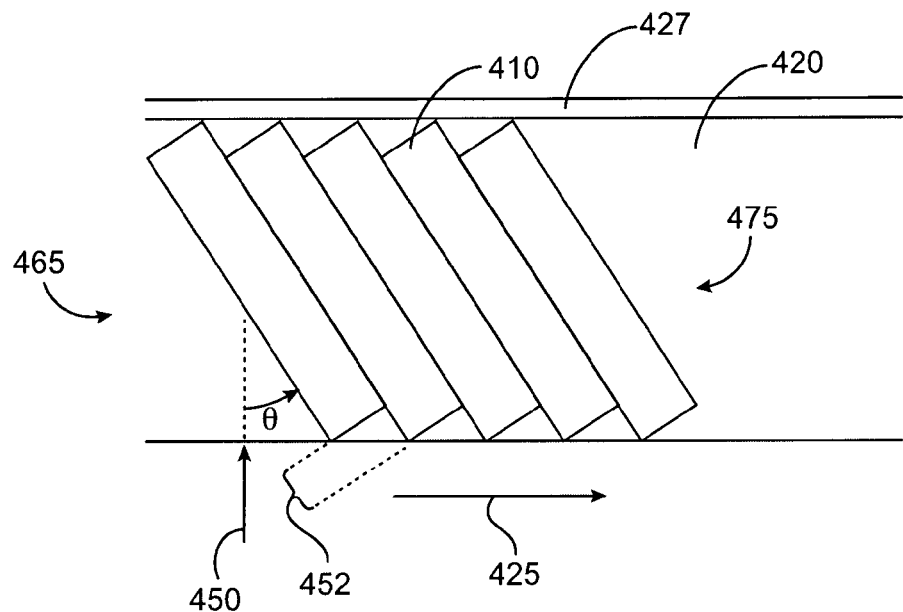
FIG. 4(b) depicts an overhead view of the fixture of FIG. 4(a).

FIGS. 4(a)-(d) illustrate schematic embodiments of the present invention. FIG. 4(a) depicts a schematic illustration of multiple packages 410 supported by a fixture 420, each package containing a stent-catheter assembly 430 that includes a stent 440 mounted on a catheter 430. Packages 410 are stacked horizontally on fixture 420. FIG. 4(b) depicts an overhead view of FIG. 4(b) of multiple packages 410 supported by a fixture 420. Additionally, fixture 420 can include a support element or side arm 427 that supports the stacked packages 410. Support element 427 can be metallic, for example, aluminum.

Packages 410 are staggered so that there is a non-overlapping portion 452 between adjacent packages. As a result, packages 410 are positioned so that the face of the packages is at an acute angle, θ, relative to the direction of the radiation beam 450. In one embodiment, packages 410 are positioned such that θ is between 35-45 degrees, or more narrowly 45 degrees. Fixture 420 in FIGS. 4(a) and 4(b) can be moved as shown by an arrow 425 past the stationary E-beam source that directs an E-beam at an angle θ to the face of packages 410. An arrow 450 shows the E-beam source in FIG. 4(b). The arrangement depicted in FIGS. 4(a) and 4(b) allows sterilization of multiple devices in one pass. Because devices are at an acute angle to beam 450 and staggered on fixture 420, radiation beam 450 penetrates several devices as fixture 420 moves as shown by arrow 425.

As shown in FIGS. 4(a)-(b), devices near a front end 465 of the stack of packages 410 have less shielding from radiation than those further behind. As a result, the radiation exposure to the devices near the front end of the stack can be different that those further behind that have more shielding since radiation exposure varies with depth of penetration and density, as described below. The difference in shielding can result in a variation in radiation exposure due to incoming radiation from device to device.

Additionally, backscattering of radiation from metallic support element or side arm 427 to packages 410 and devices contained within can increase the radiation exposure to the devices. Backscatter of radiation, such as electrons, is caused when the electrons hit a dense material (such as a metallic fixture) and are reflected back. The exposure due to backscatter can be desirable since the portions of the device closer to side arm 427 have reduced radiation exposure since radiation exposure varies with penetration depth, as described below. The backscatter of at least some radiation compensates for the reduced exposure. However, as shown in FIG. 4(a)-4(b), devices at a back end 475 of the stack of packages 410 have more shielding from the backscatter those closer to the front. The difference in shielding can result in a variation in radiation exposure from device to device due to backscatter.

In general, the thicker and/or denser a material is, the more it will scatter electrons, creating a "shadow" or lower dose area behind the dense material. In one embodiment, the densest part of fixture is placed towards the back to prevent it from shadowing other parts of the device. For example, as pictured in FIG. 5, the densest part of fixture 420 is aluminum side arm 427, which is positioned such that it is behind assemblies 410 relative to beam 450.

Figure 4C:
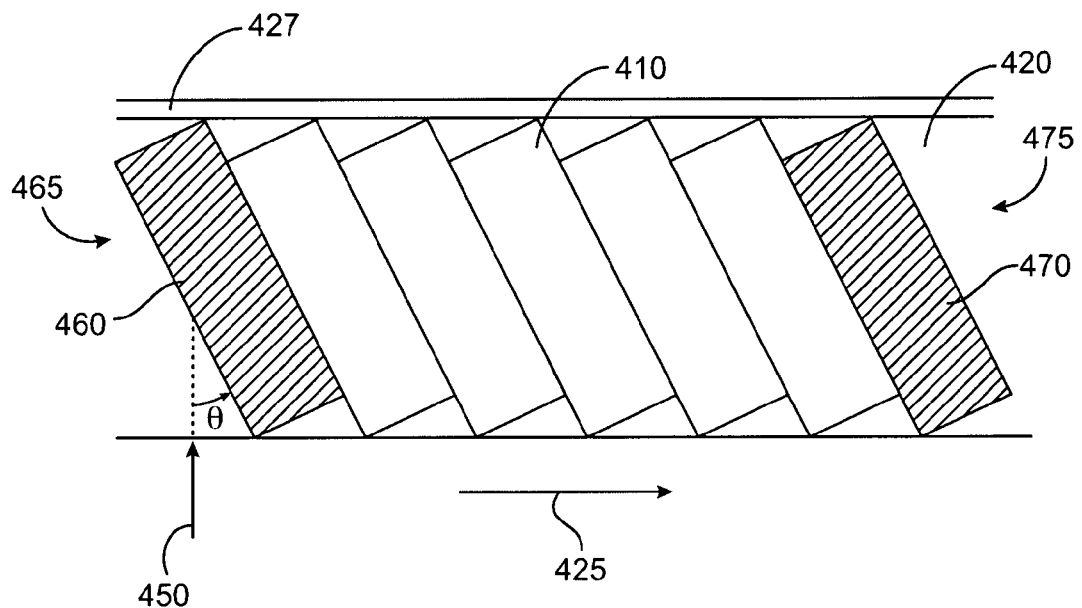
FIG. 4(c) depicts an overhead view of the fixture of FIG. 4(a) additionally including two radiation shields on the front and back of the fixture.
Figure 4D:
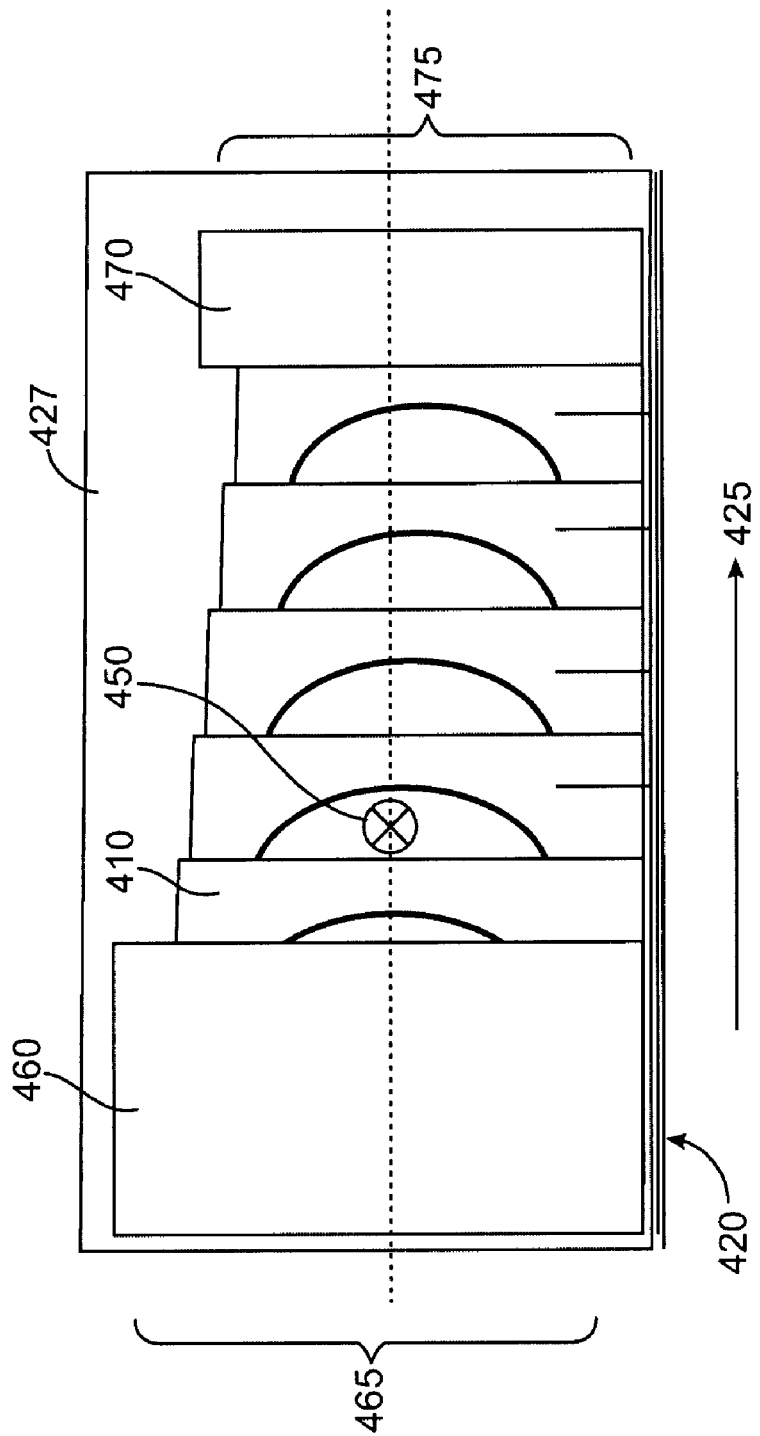
FIG. 4(d) is a schematic illustration of a front view of the fixture of FIG. 4(c).

FIG. 4(c) depicts an overhead view of a system similar to FIG. 4(a) of a multitude of packages supported by a fixture 420, additionally including two radiation shields 460 and 470 on at front end 465 and back end 475 of the stack of packages 410, respectively. FIG. 4(d) is a schematic illustration of a front view of the embodiment depicted in FIG. 4(c). In one embodiment, one or both of radiation shields 460 and 470 are composed of foam.

FIG. 4(d) is a schematic illustration of a front view of the fixture of FIG. 4(c). As depicted in FIGS. 4(c) and 4(d), radiation shields 460 and 470 are strategically positioned on front end 465 and back end 475, respectively, of the stack of devices to reduce the radiation exposure variation from device to device. Radiation shield 460 can reduce or eliminate the difference in radiation exposure between devices near front end 465 and those behind due to incoming radiation. Radiation beam 450 can be modified prior to irradiating the devices located near the front end 465 of the stack of devices on fixture 420, thereby providing greater uniformity in radiation exposure to the devices. Radiation shield 460 can act effectively as a "dummy device." In an embodiment, radiation shield 460 can provide shielding so that the devices near the front end receive the same or similar exposure from incoming radiation as devices behind. Since radiation exposure varies with thickness and density, the thickness and density of the radiation barrier can be selected to obtain a desired exposure to devices.

Radiation shield 470 is positioned on the back end of fixture 420 to shield packages 410 from backscatter of the radiation from side arm 427. Radiation shield 470 can reduce or eliminate the difference in radiation exposure between devices near back end 475 and those behind due to backscattering of radiation. Radiation backscattered from side arm 427 can be modified prior to irradiating the devices located near back end 475 of the stack of devices on fixture 420, thereby providing greater uniformity in radiation exposure to the devices. Radiation shield 475 can also act effectively as a "dummy device." In an embodiment, radiation shield 470 can provide shielding so that the devices near the back end receives the same or similar exposure from backscattered radiation as devices at the front end. The thickness and density of the radiation barrier can be selected to obtain a desired exposure to devices.

Thus, one or more radiation shields can increase the uniformity of the dose received over the multitude of devices positioned on fixture 420. All devices on fixture 420 can be adequately sterilized during one pass of radiation, which can increase throughput. Additionally, in a reduced temperature sterilization process, the cooling step between passes is eliminated in a one pass process, which also reduces process time.

Figure 5:
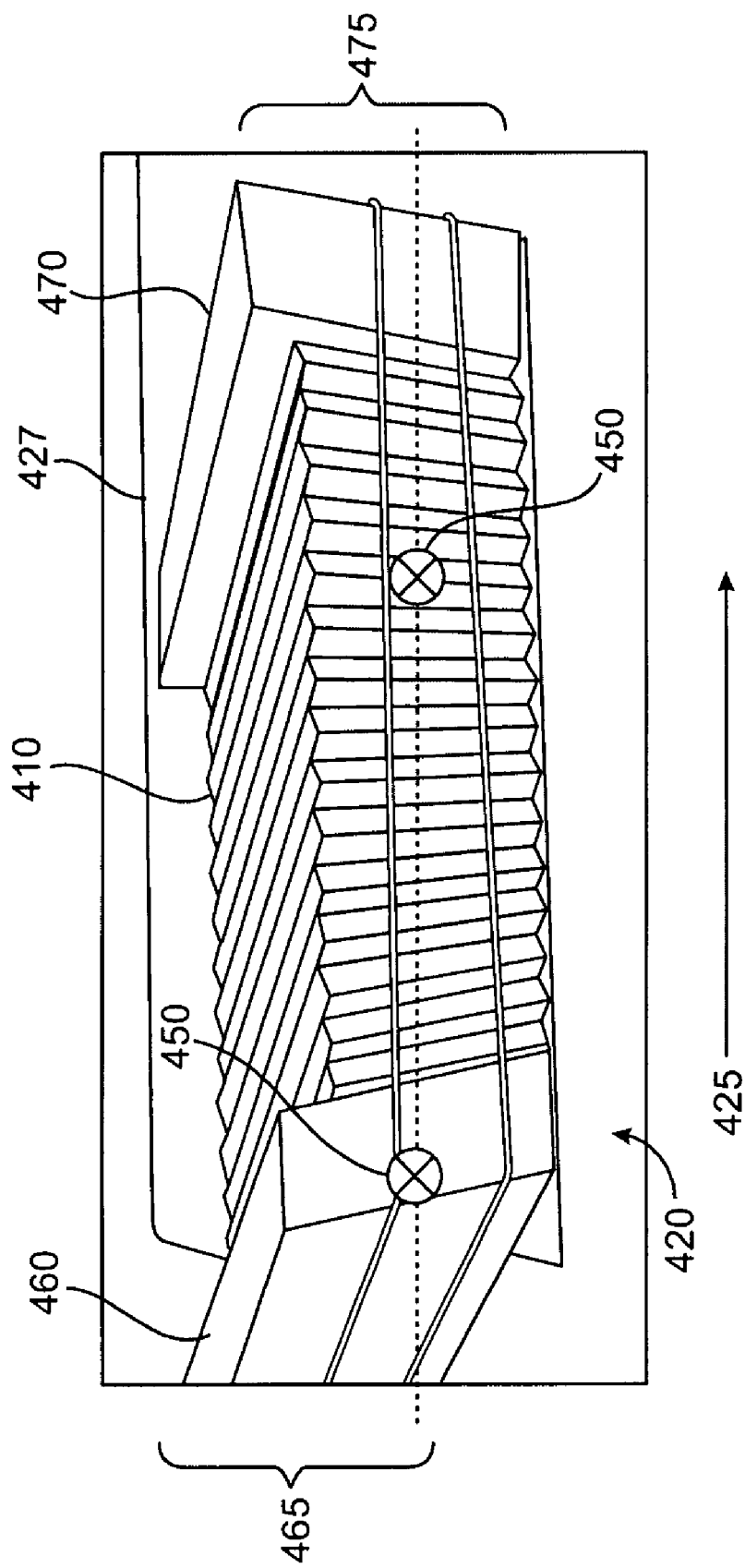
FIG. 5 depicts a photograph of multiple packages supported on a fixture and two radiation shields on the front and the back of the fixture.

FIG. 5 depicts a photograph of a fixture with a multitude of devices with radiation shield 460 and radiation shield 470. An aluminum side arm 427 behind the stacked packages 410 supports the packages. Metal side arm 427 ensures that the packages are positioned on fixture 420 at an angle.

In one embodiment, as depicted in FIG. 5, fixture 420 contains between 12-18 devices. In such embodiments, the radiation beam can penetrate through one to 8 packages, or more narrowly, the radiation beam can penetrate through five packages. It should be understood by those skilled in the art that fixture 420 can contain more or less devices, depending on the size of the device, the fixture, and the angle that the devices are positioned on the fixture.

The dose is selected according to the devices to be sterilized. For example, a desired dose for a stent can be about 25 kGy. In one embodiment a dose of incoming radiation can be set at 35-45 kGy, or more narrowly, 40 kGy. The radiation dose received a stent can be lower than the incoming radiation dose due to modification of the radiation as it passes through packaging, devices, shielding, etc., as described below. Other radiation doses can be used, depending on the device to be sterilized.

Figure 6:
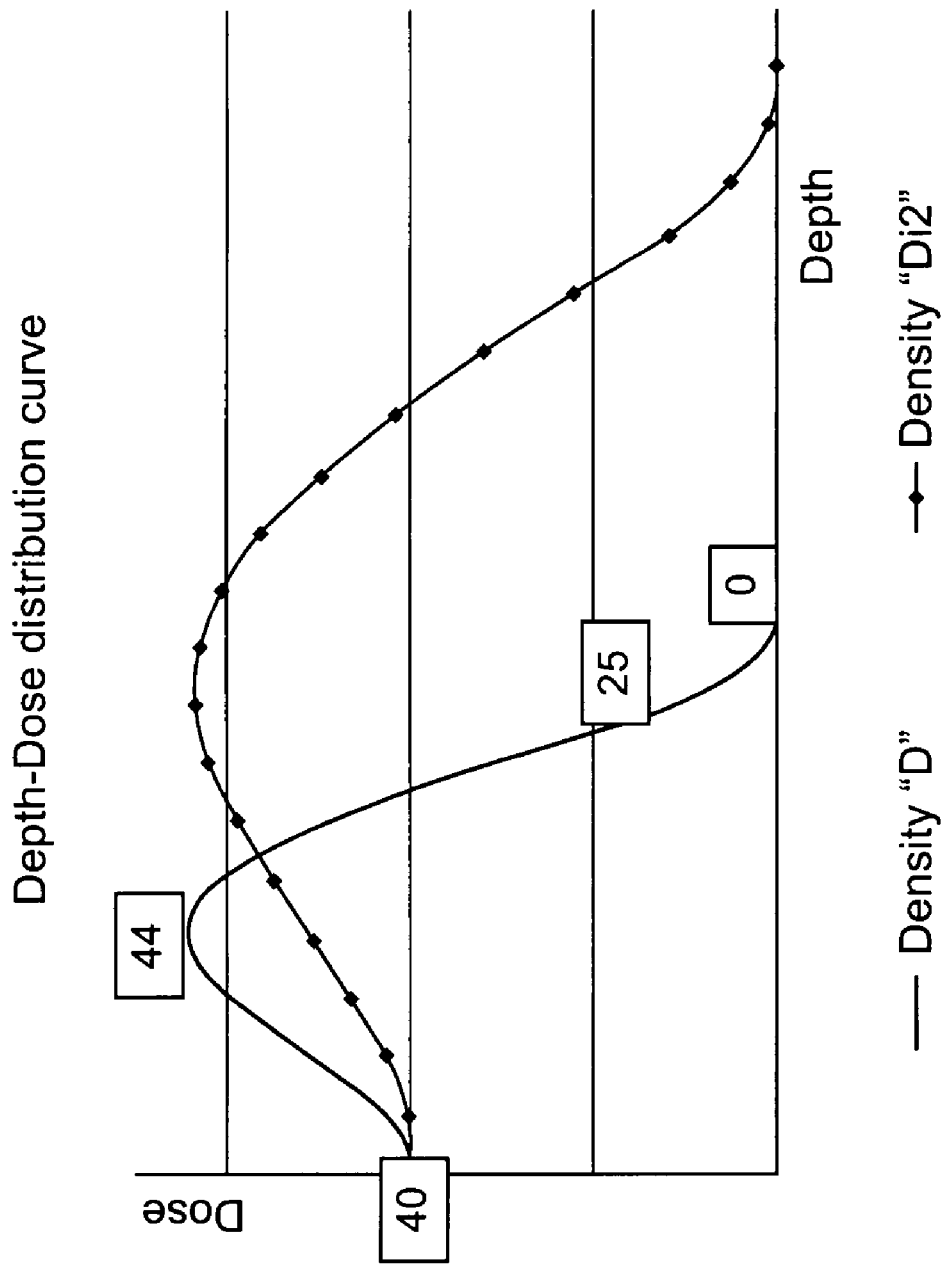
FIG. 6 depicts a depth to dose distribution curve illustrating the relationship between radiation exposure and depth of penetration of a radiation beam.

FIG. 6 depicts a depth dose distribution curve illustrating the relationship between radiation exposure and depth of penetration of the radiation beam for materials with two densities. The curve shows the dose versus the depth of a material that the electrons travel through for two densities. As depicted, the dose initially rises and then drops off. For example, if a device is irradiated with 40 kGy, the peak dose is at 44 kGy, and it eventually drops down to, for example, 25 kGy and finally to 0 kGy upon further permeation through a material. As shown in FIG. 6, the curve is shifted to larger penetration as density is decreased.

The general relationship in FIG. 6 can be used to design a fixture, arrangement of devices, and shields in a manner that devices received a desired radiation dose. The total exposure to a device can be from incoming radiation and backscattered radiation. Thus, packages can be arranged, as described above, and the thickness and density of the shields can be selected to obtain a desired radiation exposure. As discussed above, the shields can be selected to increase the uniformity of exposure from device to device. In alternate embodiments, the total exposure can be due to incoming radiation, with no exposure due to backscattering.

The curve in FIG. 6 can be manipulated by the radiation shields to obtain a desired dose level. The radiation shields having a certain density, like foam, are used to change the radiation dose to a desired level in a specific depth of irradiated packages. Increasing the density shifts the peak to a smaller depth, thus, larger depths have a smaller dose. By adding radiation shields at both ends of a fixture, as pictured in FIG. 5, the density dose curve advances to the descending portion of the curve prior to irradiating the fixtures, thereby reducing radiation absorption of the device. In this way, devices on the ends of the stack are substantially consistent with the radiation absorption of the other devices that are shielded by other devices.

Thus, radiation shields can reduce the dose of radiation that the devices are irradiated with by shifting the dose to depth curve. Since the packages are at an angle with respect to the beam, the radiation exposure varies at least as a function of "x" (FIG. 7) across the face of the device, and more generally as a function of the "x" and "y" position on the face of the device. Thus, to have the same exposure for each stent, the stents may be positioned to the same x position, or more generally at the same position on the face of the device. The position can be selected so that the stents receive a desired radiation exposure.

Figure 7:
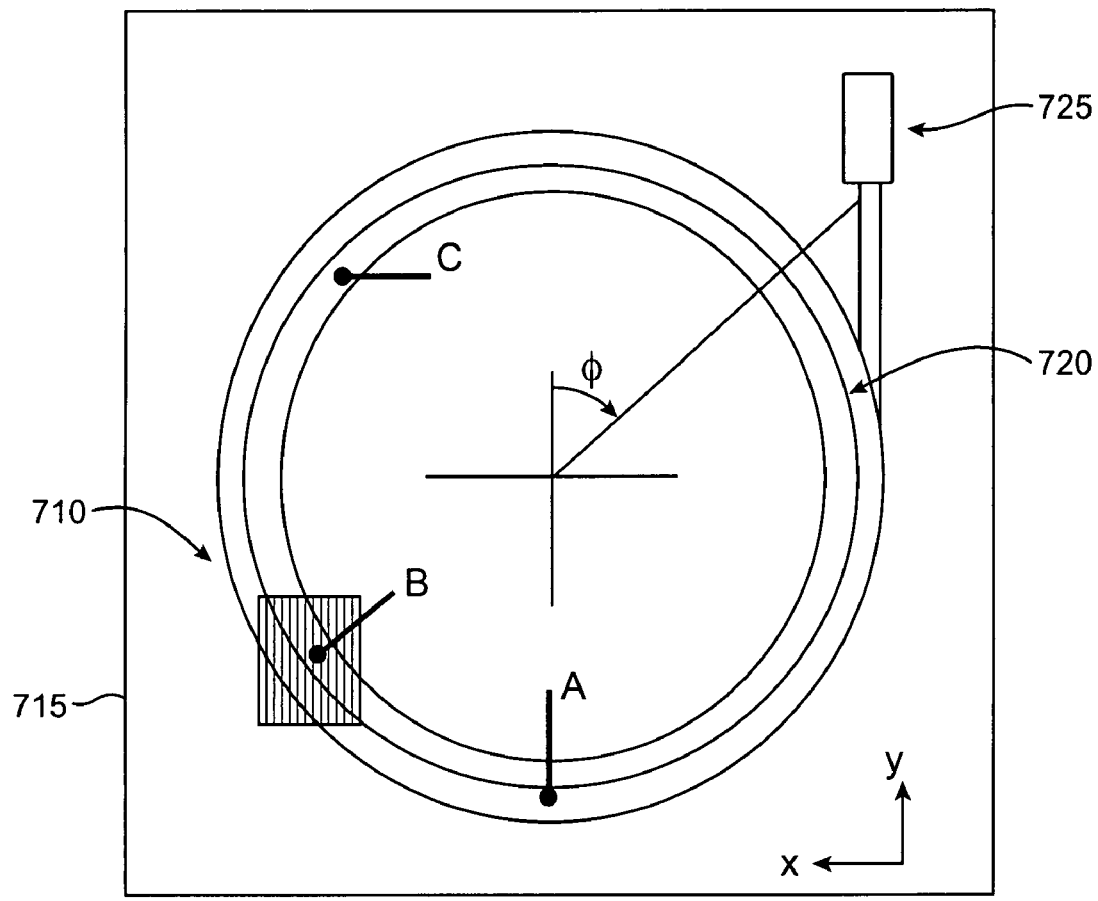
FIG. 7 depicts a package for a stent-catheter assembly, indicating three areas of the package that are measured for radiation dose mapping of a device.

As depicted in FIG. 7, a stent-catheter assembly 710 with a stent 725 disposed on a catheter 720 can be inside a storage package 715. Devices are positioned on fixture such that stents are at an angle $\phi$. In one embodiment, devices are positioned such that each stent is positioned at the same angle $\phi$ in each package to increase the uniformity of exposure to the stent from device to device. In one embodiment, stent 725 may be positioned in a package 715 on a fixture such that stent 725 is at a 7 o'clock ($\phi=216°$) position when viewing stent 710 from the front of the fixture. Stents may be positioned within package 715 on the fixture in other angles, such that it is between 1 and 3 (φ=36-108°), or more narrowly, at a 2 o'clock (φ=72°) position when viewing stent 725 from the front of fixture.

At various parts of the stent, radiation dose requirements may differ. However, when sterilizing multiple stent-catheter assemblies, it is preferable that the radiation dose at the stent not vary substantially from stent to stent since E-beam exposure affects properties of a material. The radiation dose received by a stent should be within a narrow range from stent to stent. At the catheter 720, a tolerance for a variation in radiation exposure is higher. The radiation exposure, for example, can be between at 20-50 kGy because the catheter is more robust than the stent for example. In contrast, the performance of a balloon, over which a stent is disposed, is much more vulnerable to degradation, thus it is desirable for its exposure to be at less than 40 kGy. Performance of stent 710 and balloon 725 are more sensitive to changes in properties, and thus, radiation exposure. Performance of catheter 720 is less sensitive to various properties, so a greater variation of radiation exposure for the catheter is more tolerable.

Dose mapping may be used to monitor the range of radiation dose received by selected portions of irradiated devices. Dose mapping refers to measuring radiation exposure at specific areas of an irradiated package and device within the package. FIG. 7 depicts three areas A, B, and C where the radiation may be measured.

Figure 8:
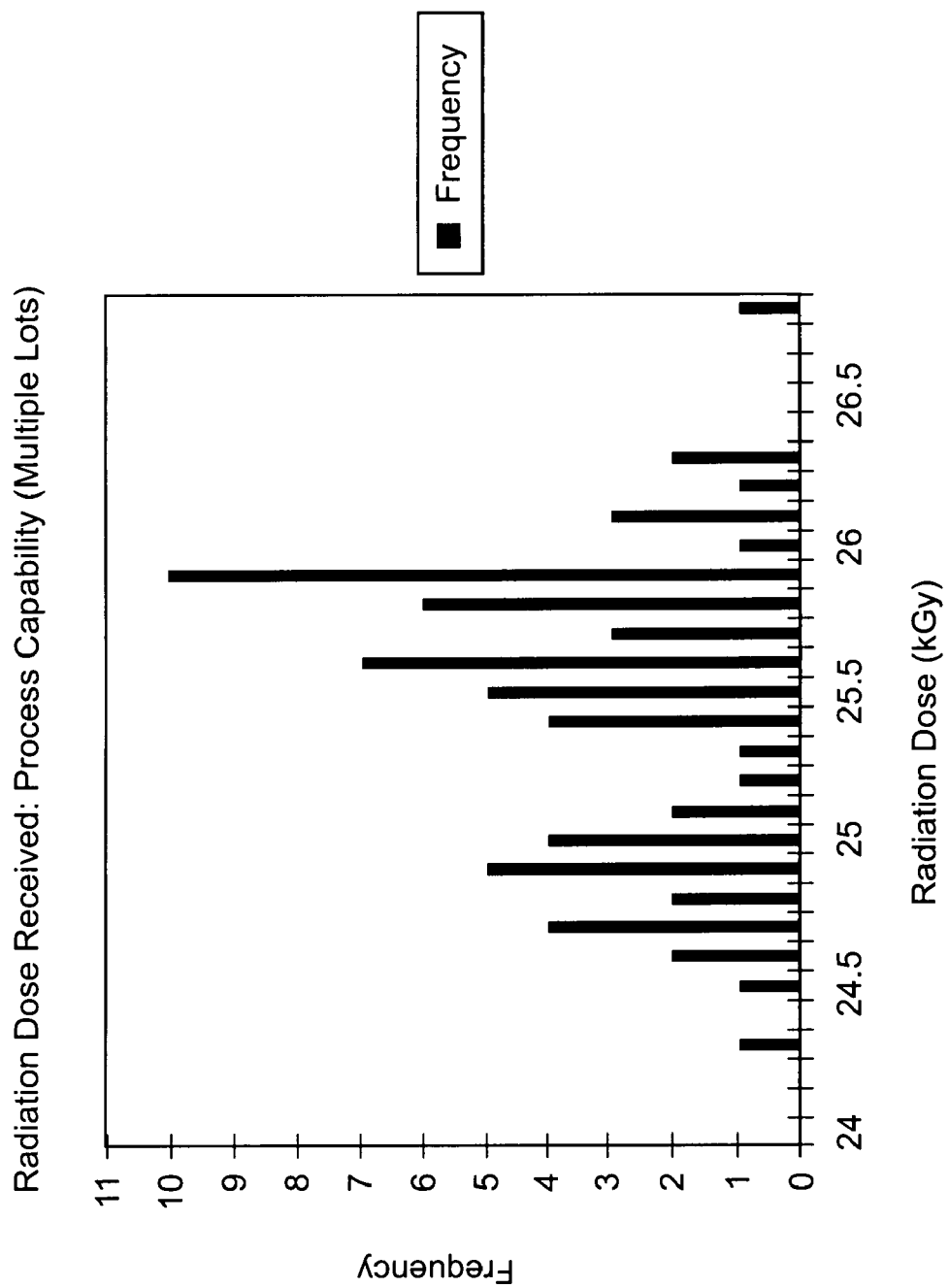
FIG. 8 depicts a chart illustrating the radiation dose received by multiple lots of chipboard boxes, each containing a stent-catheter assembly.

FIG. 8 depicts a chart illustrating the radiation dose received by multiple lots of chipboard boxes, each containing a stent-catheter assembly. The system for sterilization is as depicted in FIG. 5. Each lot corresponds to 15 chipboard boxes that are exposed to one pass of radiation. The radiation dose corresponds to the radiation exposure at a particular region of each stent in each lot. The radiation dose received by a particular area of the stents that are packaged and irradiated are compared to multiple lots as illustrated by the graph. As indicated, the spread of radiation ranges from 24.3 to 26.8, with the frequency of doses being much higher in the 24.7 to 26.2 range. Thus, most devices are of a very narrow range of about 24 to 26 KGy. Providing a narrow dose range prevents irradiating devices outside their required SAL, outside of a defined tolerance, or both. The likelihood of exposing a par of a device to radiation outside a desired SAL is reduced.

In one embodiment, devices are irradiated at a reduced temperature and "Targeted Dose" process. The device may be cooled prior to, during, or after sterilization. The stent can be cooled in a variety of ways, including, but not limited to, cooling the stent in a freezer, blowing a cold gas on the stent, placing the stent in proximity to a cold medium such as ice, dry ice, freezable gel, liquid nitrogen, etc.

The storage package for the implantable medical device, such as a stent, can be designed in any convenient form, shape and size that permits the effective enclosure of a stent contained therein. For example, a flexible pouch made from a polymer, glass, ceramic, metallic substance, or a combination thereof. Package can be made from metal, foam, plastic etc. For example, a material with micro-voids, such as foam, or particles, can scatter E-beam radiation which results in the more even distribution. "Foam" can refer to a polymer foam, for example, polystyrene foam such as Styrofoam from Dow Chemical Company, Midland, Mich. Thus, the package material can also be made of a material that distributes radiation more uniformly such as foam.

The package may be compact and shaped so as to minimize storage space occupied by the package. For example, without limitation, the package can be in the shape of a tube, box or a pouch. In one embodiment, the package can have a rectangular cross-section with a width between 8 in and 12 in and a length between 10 in and 13 in. Also, depending on the types of substance(s) used to construct the package, the package can be of various degrees of rigidity or flexibility.

Such packages can be stored individually or stored together with other packaged stents. For example, a pouch can be disposed in a box, such as chipboard box. The chipboard box can then be stored individually or along with a number of similar or identical packages including stents.

The package may be made of a metallic substance, the package for example can be formed of a metallic film. Suitable examples of films include, but are not limited to, gold, platinum, platinum/iridium alloy, tantalum, palladium, chromium, and aluminum. Suitable materials for the package may also include oxides of the above-mentioned metals, for example, aluminum oxide. Medical storage packages may be obtained from, for example, Oliver Devices Company of Grand Rapids, Mich.

A polymer for use in fabricating an implantable medical device, such as a stent, can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes. For stents made from a biodegradable polymer, the stent is intended to remain in the body for a duration of time until its intended function of, for example, maintaining vascular patency and/or drug delivery is accomplished.

The device may also be made of a metallic material or an alloy such as, but not limited to, a biodegradable metal.

The device may also include a drug or active agent that can include, but is not limited to, any substance capable of exerting a therapeutic, prophylactic, or diagnostic effect. The drugs for use in the implantable medical device, such as a stent or non-load bearing scaffolding structure may be of any or a combination of a therapeutic, prophylactic, or diagnostic agents. The drug can be incorporated in a polymer substrate or in a coating on the substrate that includes the drug within a polymer carrier.

While particular embodiments of the present invention have been shown and described, it will be obvious to those skilled in the art that changes and modifications can be made without departing from this invention in its broader aspects.

EXAMPLES

Three experiments were performed to map the dose distribution on a biodegradable stent and delivery system using a fixture as depicted in FIG. 4(*b*). For each of the experiments, 15 packages containing stents were stacked onto the aluminum fixture such that the packages were angled 45° to the trajectory of the radiation beam. The delivered dose at a particular region of the stent in each package was measured.

In the first experiment, no radiation shield of foam was positioned at the front end or back end of the fixture. The delivered dose range absorbed by the stents ranged from 15.88 to 20.96 kGy, or a ratio of 1:32.

In the second experiment, a radiation shield of foam was positioned at the front end of the fixture. The results indicated a reduction in the dose spread absorbed by the stents ranged from 22.49 to 25.48 kGy, or a ratio of 1:14. It is believed that the backscatter from the aluminum fixture at the back end was contributing to scatter, and thus, the spread.

In the third experiment, a radiation shield of foam was added to both the front end and the back end of the fixture. In other words, a radiation shield was positioned on both ends of the stack of devices. On the back end of the fixture, the spread of radiation absorbed by the stents ranged from 23.89 to 26.6 kGy, or a ratio of 1:11. This experiment was repeated to confirm the results, having a ratio of 1:05. Thus, a radiation shield positioned at both ends of the stack of devices on the fixture provided the narrowest spread of radiation dose among the devices positioned on the fixture.

What is claimed is:

1. A method of radiation sterilizing a plurality of stent-catheter assemblies, the method comprising:
Positioning a plurality of stent-catheter assemblies on a fixture, each of the stent catheter assemblies being arranged in a planar configuration and disposed in corresponding planar packaged supported on the fixture, wherein the packages are stacked horizontally on the fixture, and wherein the stents of the assemblies are positioned at a position in each package such that the stents are exposed to the same or substantially the same radiation; and
Exposing the packages to an incoming radiation beam, the radiation beam being at an acute angle to the planes of the planar configuration of the assemblies, wherein the packages are arranged such that a front end of the stack faces the radiation beam and a back end of the stack faces away from the radiation beam, wherein a radiation shield is positioned at the front end of the stack to reduce radiation exposure to selected assemblies adjacent the front end from the incoming radiation.

2. The method according to claim 1, wherein the radiation beam comprises an e-beam radiation beam.

3. The method according to claim 1, wherein the planar packages in the stack are staggered along an edge of the stack facing the radiation beam.

4. The method according to claim 1, wherein radiation shield is positioned and the properties of the radiation shield are selected such that variation in radiation exposure to the selected assemblies from incoming radiation and the other assemblies in the stack is reduced, substantially eliminated, or eliminated.

5. The method according to claim 1, wherein the stents of the assemblies are positioned at a position in each package such that the stents are exposed to the same or substantially the same radiation.

6. The method according to claim 1, wherein each of the stent catheter assemblies are arranged in a coiled configuration.

7. The method according to claim 1, wherein the incoming radiation is 35-45 KGy and the stent in each of the assemblies is positioned at 36°-108° in the coiled configuration.

8. The method according to claim 1, wherein the acute angle is 35°-45°.

9. The method according to claim 1, wherein exposing the packages to a radiation beam comprises movement of the fixture with respect to the incoming radiation beam.

10. The method according to claim 9, wherein the assemblies are sufficiently sterilized after one movement of the fixture with respect to the incoming radiation beam.

11. The method according to claim 1, wherein the assemblies are cooled prior to, during or after positioning the assemblies on the fixture.

12. A method of radiation sterilizing a plurality of stent-catheter assemblies, the method comprising:
Positioning a plurality of stent-catheter assemblies on a fixture, each of the stent catheter assemblies being arranged in a planar configuration and disposed in corresponding planar packages supported on the fixture, wherein the packaged are stacked horizontally on the fixture, and wherein the stents of the assemblies are positioned in each package such that the stents are exposed to the same or substantially the same radiation; and
Exposing the packages to an incoming radiation beam, the radiation beam being at an acute angle to the planes of the planar configuration of the assemblies, wherein the packages are arranged such that a front end of the stack faces the radiation beam and a back end of the stack faces away from the radiation beam, wherein a radiation shield is positioned at the back end of the stack to reduce backscatter of radiation from a support element of the fixture to selected assemblies adjacent the back end.

13. The method according to claim 12, wherein the radiation shield is positioned and the properties of the radiation shield are selected such that a variation in radiation exposure from backscattered radiation to the selected assemblies and the other assemblies in the stack is reduced, substantially eliminated, or eliminated.

14. A method of radiation sterilizing a plurality of medical devices, the method comprising:
positioning a plurality of medical devices on a fixture; and
exposing the devices to an incoming radiation beam through movement of the plurality of devices with respect to a radiation source, wherein the number of devices through which the radiation beam passes varies with the movement, wherein a radiation shield is positioned such that a variation in radiation exposure among the medical devices from incoming or backscattered radiation is reduced.

15. The method according to claim 14, wherein the radiation shield is positioned between a support element of the fixture and selected devices, the radiation shield reducing radiation exposure from backscattering from the support element to the selected devices.

16. The method according to claim 14, wherein the radiation shield is positioned between the incoming radiation beam and selected devices, the radiation shield modifying radiation exposure from the incoming radiation to the selected devices.

17. The method according to claim 14, wherein the radiation shield comprises foam.

18. The method according to claim 14, wherein the devices are cooled prior to, during or after positioning the devices on the fixture.

19. The method according to claim 14, wherein a selected portion of each of the devices are positioned such that the selected portion of each of the devices is exposed to the same or substantially the same radiation.

20. A method of radiation sterilizing a plurality of medical devices, the method comprising:
only one cooling step, wherein in the only cooling step a plurality of medical devices are cooled;
positioning the plurality of medical devices on a fixture;
positioning a radiation shield relative to the medical devices such that a variation in radiation exposure among the medical devices from incoming or backscattered radiation is reduced; and
only one sterilizing step, wherein in the only sterilizing step there is only one pass of a radiation beam to expose the plurality of medical devices to radiation.

21. The method according to claim 20, wherein the radiation shield is positioned between a support element of the fixture and selected devices, the radiation shield reducing radiation exposure from backscattering from the support element to the selected devices.

22. The method according to claim 20, wherein the radiation shield is positioned between the incoming radiation beam and selected devices, the radiation shield modifying radiation exposure from the incoming radiation to the selected devices.

23. The method according to claim 20, wherein the radiation shield comprises foam.

24. A method of sterilizing a stack of packages of medical devices, the method comprising:
    placing a stack of packages of medical devices horizontally on a fixture having a support element, the step of positioning the stack including:
        placing the stack between a radiation source and the support element of the fixture,
        staggering the stack of packages horizontally so that there is a non-overlapping portion between adjacent packages, and
        positioning the stack of packages so that faces of the packages are at an acute angle relative to a radiation beam from the radiation source;
    positioning a radiation shield relative to the stack of packages such that a variation in radiation exposure among the medical devices from incoming or backscattered radiation is reduced; and
    exposing the packages to an incoming radiation beam.

25. The method of claim 24, wherein each medical device is placed in the same horizontal and vertical positions within the package.

26. The method of claim 25, wherein the step of positioning a radiation shield includes positioning a radiation shield at the front end of the stack to reduce radiation exposure to one or more packages in the front end from incoming radiation.

27. The method of claim 26, wherein the step of positioning a radiation shield includes positioning a radiation shield at the back end of the stack to reduce backscatter of radiation from the support element of the fixture to one or more packages in the back end of the stack.

28. The method of claim 27, wherein the thickness and/or density of at least one of the radiation shields are varied to obtain a desired exposure to the packages.

29. The method of claim 24, wherein the step of positioning a radiation shield includes positioning a radiation shield at the front end of the stack to reduce radiation exposure to one or more packages in the front end from incoming radiation.

30. The method of claim 29, wherein the step of positioning a radiation shield includes positioning a radiation shield at the back end of the stack to reduce backscatter of radiation from the support element of the fixture to one or more packages in the back end of the stack.

31. The method of claim 30, wherein the thickness and/or density of at least one of the radiation shields are varied to obtain a desired exposure to the packages.

32. The method of claim 31, wherein the packages are exposed to the incoming radiation beam to irradiate the packages substantially uniformly.

33. The method of claim 24, wherein the step of positioning a radiation shield includes positioning a radiation shield at the back end of the stack to reduce backscatter of radiation from the support element of the fixture to one or more packages in the back end of the stack.

34. The method of claim 33, wherein the thickness and/or density of the radiation shield is varied to obtain a desired exposure to the packages.

35. The method of claim 34, wherein the packages are exposed to the incoming radiation beam to irradiate the packages substantially uniformly.

36. The method of claim 24, wherein the packages are exposed to the incoming radiation beam to irradiate the packages substantially uniformly.

37. A method of sterilizing a stack of packages of medical devices, the method comprising:
    Placing a stack of packages of medical devices horizontally on a fixture having a support element, the step of positioning the stack including:
        Placing the stack between a radiation source and the support element of the fixture,
        Staggering the stack of packages horizontally so that there is a non-overlapping portion between adjacent packages, and
        Positioning the stack of packages so that faces of the packages are at an acute angle relative to a radiation beam from the radiation source,
        Wherein each medical device is not placed in the middle of the package, and wherein each medical device is placed in the same horizontal and vertical positions within the package;
    Exposing the packages to an incoming radiation beam, and positioning a radiation shield relative to the stack of packages such that a variation in radiation exposure among the medical devices from incoming or backscattered radiation is reduced.

38. The method of claim 37, wherein the step of positioning a radiation shield includes positioning a radiation shield at the front end of the stack to reduce radiation exposure to one or more packages in the front end from incoming radiation.

39. The method of claim 38, wherein the step of positioning a radiation shield includes positioning a radiation shield at the back end of the stack to reduce backscatter of radiation from the support element of the fixture to one or more packages in the back end of the stack.

40. The method of claim 39, wherein the thickness and/or density of at least one of the radiation shields are varied to obtain a desired exposure to the packages.

41. The method of claim 37, wherein the step of positioning a radiation shield includes positioning a radiation shield at the back end of the stack to reduce backscatter of radiation from the support element of the fixture to one or more packages in the back end of the stack.

42. The method of claim 41, wherein the thickness and/or density of at least one of the radiation shields are varied to obtain a desired exposure to the packages.

43. A method of sterilizing a stack of packages of stents, the method comprising:
    placing a stack of packages of stents horizontally on a fixture having a support element, the step of positioning the stack including:
        placing the stack between a radiation source and the support element of the fixture,
        staggering the stack of packages horizontally so that there is a non-overlapping portion between adjacent packages, and
        positioning the stack of packages so that faces of the packages are at an acute angle relative to a radiation beam from the radiation source,
        wherein each stent is not placed in the middle of each package, and wherein each stent is placed in the same horizontal position within the package, each stent is placed in the same vertical position within the package, or each stent is placed in the same horizontal and vertical positions within the package;

positioning a radiation shield relative to the stack of packages such that a variation in radiation exposure among the stents from incoming or backscattered radiation is reduced, wherein the step of positioning a radiation shield includes positioning a radiation shield at the front end of the stack to reduce radiation exposure to one or more packages in the front end from incoming radiation, and positioning a radiation shield at the back end of the stack to reduce backscatter of radiation from the support element of the fixture to one or more packages in the back end of the stack, wherein the thickness and/or density of at least one of the radiation shields are varied to obtain a desired exposure to the packages; and exposing the packages to an incoming radiation beam, wherein the packages are irradiated substantially uniformly.

44. A method of sterilizing a stack of packages of stents, the method comprising:

placing a stack of packages of stents horizontally on a fixture having a support element, the step of positioning the stack including:

placing the stack between a radiation source and the support element of the fixture, staggering the stack of packages horizontally so that there is a non-overlapping portion between adjacent packages, and positioning the stack of packages so that faces of the packages are at an acute angle relative to a radiation beam from the radiation source;

positioning a radiation shield relative to the stack of packages such that a variation in radiation exposure among the stents from incoming or backscattered radiation is reduced, wherein the step of positioning a radiation shield includes positioning a radiation shield at the front end of the stack to reduce radiation exposure to one or more packages in the front end from incoming radiation, and positioning a radiation shield at the back end of the stack to reduce backscatter of radiation from the support element of the fixture to one or more packages in the back end of the stack, wherein the thickness and/or density of at least one of the radiation shields are varied to obtain a desired exposure to the packages; and exposing the packages to an incoming radiation beam, wherein the packages are irradiated substantially uniformly.

45. A method of sterilizing a stack of packages of stents, the method comprising:

placing a stack of packages of stents horizontally on a fixture having a support element, the step of positioning the stack including:

placing the stack between a radiation source and the support element of the fixture, staggering the stack of packages horizontally so that there is a non-overlapping portion between adjacent packages, and positioning the stack of packages so that faces of the packages are at an acute angle relative to a radiation beam from the radiation source, wherein each stent is not placed in the middle of each package, and wherein each stent is placed in the same horizontal and vertical positions within the package;

positioning a radiation shield relative to the stack of packages such that a variation in radiation exposure among the stents from incoming or backscattered radiation is reduced, wherein the step of positioning a radiation shield includes positioning a radiation shield at the front end of the stack to reduce radiation exposure to one or more packages in the front end from incoming radiation, and positioning a radiation shield at the back end of the stack to reduce backscatter of radiation from the support element of the fixture to one or more packages in the back end of the stack, wherein the thickness and/or density of at least one of the radiation shields are varied to obtain a desired exposure to the packages; and exposing the packages to an incoming radiation beam, wherein the packages are irradiated substantially uniformly.

\* \* \* \* \*